United States Patent
Kyriakou

(10) Patent No.: US 9,123,148 B2
(45) Date of Patent: Sep. 1, 2015

(54) METHOD FOR GENERATING A SOLID MODEL OF A HEART AND ASSOCIATED C-ARM X-RAY EQUIPMENT

(71) Applicant: Yiannis Kyriakou, Spardorf (DE)

(72) Inventor: Yiannis Kyriakou, Spardorf (DE)

(73) Assignee: SIEMENS AKTIENGESELLSCHAFT, Munich (DE)

(*) Notice: Subject to any disclaimer, the term of this patent is extended or adjusted under 35 U.S.C. 154(b) by 92 days.

(21) Appl. No.: 14/010,813

(22) Filed: Aug. 27, 2013

(65) Prior Publication Data
US 2014/0064593 A1    Mar. 6, 2014

(30) Foreign Application Priority Data

Aug. 29, 2012   (DE) .......................... 10 2012 215 294

(51) Int. Cl.
*G06K 9/00* (2006.01)
*G06T 17/00* (2006.01)
(Continued)

(52) U.S. Cl.
CPC .............. *G06T 17/00* (2013.01); *A61B 5/0456* (2013.01); *A61B 6/4085* (2013.01); *A61B 6/4441* (2013.01); *A61B 6/503* (2013.01); *A61B 6/5205* (2013.01); *A61B 6/541* (2013.01); *G06T 11/008* (2013.01); *A61B 6/583* (2013.01); *G06T 2211/412* (2013.01)

(58) Field of Classification Search
CPC . G06T 17/00; G06T 11/008; G06T 2211/412; A61B 6/4085; A61B 6/4441; A61B 6/503; A61B 6/0456
USPC .......................................... 382/132, 154, 275
See application file for complete search history.

(56) References Cited

U.S. PATENT DOCUMENTS 7,940,976 B2 *  5/2011  Ozawa ........................... 382/132
7,986,822 B2 *  7/2011  Hall et al. ...................... 382/128
(Continued)

FOREIGN PATENT DOCUMENTS

DE    102008052685 A1    5/2010
DE    102009032060 A1    1/2011

OTHER PUBLICATIONS

AXIOM Sensis—Hemodynamic and Electrophysiology Information and Recording System for Cardiac Cathlabs; Siemens Medical Solutions; AXIOM Sensis—Hemodynamic and Electrophysiology Information and Recording System for Cardiac Cathlabs; © 2005 Siemens Medical Solutions Order No. A91001-M1400-G907-4-7600 Printed in Germany AX CRM NA 02053; 2005.
(Continued)

*Primary Examiner* — Gregory M Desire

(57) ABSTRACT

A method for generating a solid model of a heart in a predetermined phase of its periodic pumping movement is proposed. During a single C-arm rotation of a C-arm X-ray unit an electrocardiogram signal with consecutive RR intervals is observed by an EKG trigger. In each RR interval a digital X-ray image is generated by EKG triggering of the C-arm X-ray unit as soon as a time difference between the current phase and the predetermined phase is less than a predetermined value. For each of the X-ray images in addition a parameter influencing the geometry of the C-arm X-ray unit is ascertained. The solid model is generated from several of the X-ray images. At least one X-ray image is selected from each RR interval and for each of the selected X-ray images a projection data set for the calculation of the solid model is ascertained by the ascertained parameter.

14 Claims, 6 Drawing Sheets

(51) Int. Cl.
*G06T 11/00* (2006.01)
*A61B 6/00* (2006.01)
*A61B 5/0456* (2006.01)

(56) References Cited

U.S. PATENT DOCUMENTS

| | | | |
|---|---|---|---|
| 8,233,682 B2 * | 7/2012 | Fessler et al. | 382/131 |
| 8,625,862 B2 * | 1/2014 | Sakaguchi | 382/128 |
| 2006/0133564 A1 * | 6/2006 | Langan et al. | 378/8 |
| 2010/0045696 A1 * | 2/2010 | Bruder et al. | 382/131 |
| 2010/0104164 A1 * | 4/2010 | Bartal et al. | 382/132 |
| 2010/0310144 A1 * | 12/2010 | Chen et al. | 382/132 |
| 2011/0164721 A1 * | 7/2011 | Jank et al. | 378/4 |
| 2014/0064593 A1 * | 3/2014 | Kyriakou | 382/132 |

OTHER PUBLICATIONS

Lauritsch Günter et al.; "Towards Cardiac C-Arm Computed Tomography", IEEE Transactions on Medical Imaging, vol. 25, No. 7, Jul. 7, 2006, pp. 922-934.

Y Kyriakou, R M Lapp, L Hillebrand, D Ertel and WA Kalender "Simultaneous misalignment correction for approximate circular cone-beam computed tomography", Phys. Med. Biol. 53, 2008, pp. 6267-6289; 2008.

* cited by examiner

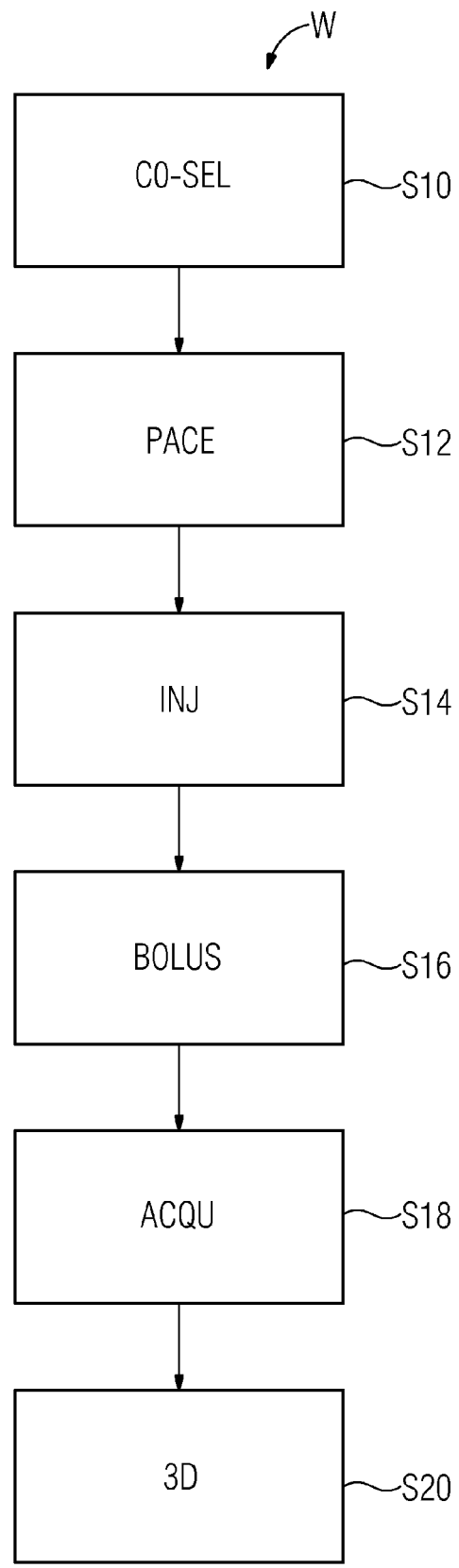

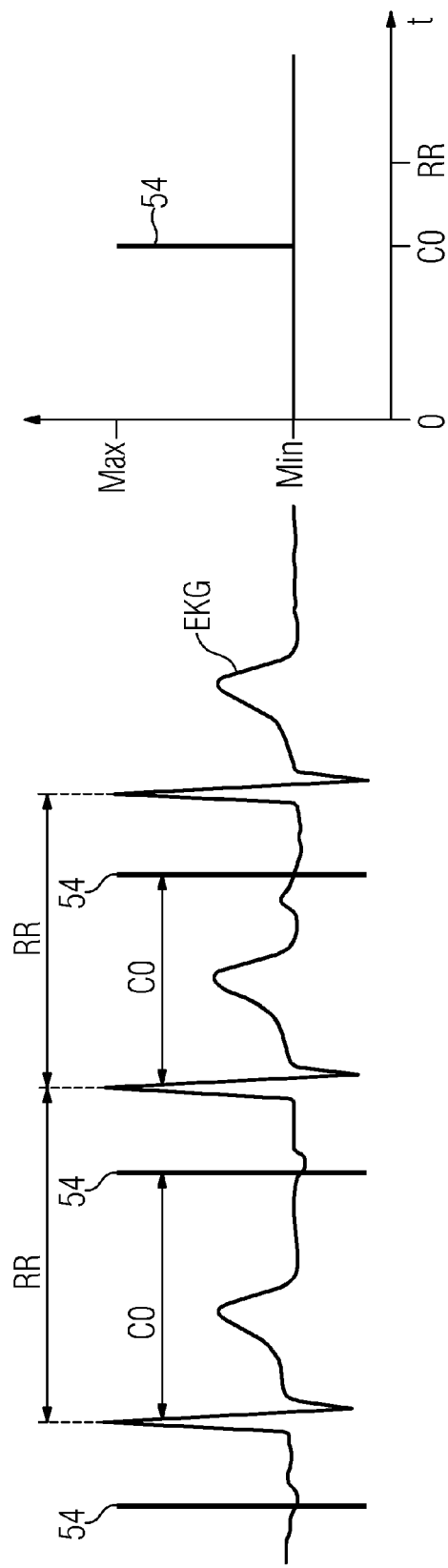

METHOD FOR GENERATING A SOLID MODEL OF A HEART AND ASSOCIATED C-ARM X-RAY EQUIPMENT

CROSS REFERENCE TO RELATED APPLICATIONS

This application claims priority to German application No. 10 2012 215 294.6 DE filed Aug. 29, 2012, the entire content of which is hereby incorporated herein by reference.

FIELD OF INVENTION

The invention relates to a method for generating a solid model of a heart in a predetermined phase of its periodic pumping movement. In accordance with the method, the solid model is generated from X-ray images which are generated by means of a C-arm X-ray unit. The invention also includes corresponding C-arm X-ray equipment with a C-arm X-ray unit.

BACKGROUND OF INVENTION

A solid model describes the mapped organ in the form of 3D-image data in which information on one of its material characteristics is given for individual volume elements (voxels) of the organ. An individual volume element may, for example, represent a rectangular-shaped section of the organ. The section may correspond to a volume of e.g. one cubic millimeter. The information for each volume element is obtained from 2D image data of the X-ray images which can be obtained with a 2D X-ray detector of the C-arm X-ray unit. The trajectory of the X-ray beams back to the X-ray focus of the X-ray source of the C-arm X-ray unit is reproduced by each pixel (picture element) of the X-ray detector. A possible algorithm for this is the sufficiently well-known backprojection, in particular the filtered backprojection, for example, of the Feldkamp type.

A C-arm X-ray unit is now characterized in that the X-ray source on the one hand and the 2D X-ray detector on the other hand are arranged at the ends of a C-shaped, rotatable metal arm. By rotating the C-arm around the body of a patient, the X-ray images which are necessary for the calculation of the voxel-based solid model of an organ of the body can be generated from various projection directions.

However, for this calculation a special feature of C-arm X-ray equipment must be noted compared with an X-ray scanner with a gantry. The C-arm displays significantly less rigidity than a gantry. The C-arm is deformed as a result of the net weight of the C-arm and the weight of the X-ray source and of the X-ray detector as well as by centrifugal forces during the C-arm rotation. This results in a different geometry of the C-arm X-ray unit for every X-ray image depending on the orientation of the C-arm and its rotational speed. A different geometry must therefore be taken as the basis for the calculation of the trajectories of the X-rays for each X-ray image.

Due to the complexity of the influences, reliance on calibration is necessary here. This is performed by means of a calibration body which can, for example, be a water-filled ball. Several X-ray images are generated by the calibration body from different projection directions. In this connection, the C-arm is moved at a predefined rotational speed around the calibration body at a predefined angle of rotation to be traversed. The X-ray images are then generated from respective predefined projection angles. The guidelines for the rotational speed, the total angle of rotation traversed and the individual projection angles for the images together define an imaging protocol for the C-arm X-ray unit.

A solid model of the calibration body is then calculated from the X-ray images. Based on the shape of the solid model of the ball, projection data can then be ascertained for the individual X-ray images, by means of which a distortion-free image of the calibration body is obtained in the solid model. Such projection data can, for example, be provided in the form of a projection matrix by means of which the 2D image data of the X-ray images is processed within the framework of a backprojection. Generally speaking, the projection data describes the trajectories of the X-rays. A projection data set for an X-ray image thus determines how the 2D image data of the X-ray image is to be introduced into the solid model.

If a solid model is now subsequently generated from a body of a patient by means of the same C-arm X-ray unit and in this connection the same imaging protocol is traversed to obtain the X-ray images as was used for calibration by means of the calibration body, then the projection data can also be re-used. In this connection it is therefore customary to save several imaging protocols for a C-arm X-ray unit and to have the projection data sets ready for each imaging protocol.

However, in connection with the generation of a solid model of a heart, a problem exists in that the heart moves periodically. A (static) 3D solid model can only represent a particular movement phase of the heart. A common specification of such a movement phase, or phase for short, is the percentage of the RR interval, in other words, for example, 70% RR. The RR interval indicates the period of time between two contractions of the ventricles of the heart. As is known, in an electrocardiogram the start of the contraction of the ventricle appears as a so-called R-wave. Correspondingly, the time lag between two R-waves corresponds to the RR interval.

With a C-arm X-ray unit it is simply not possible to now monitor an electrocardiogram signal and to generate an X-ray image whenever the heart is in the desired phase of its periodic pumping movement, in other words, for example, at 70% RR. Such EKG triggering by an EKG trigger in particular means that the trigger times for the X-ray images are dependent on the heartbeat. For this reason, however, a prepared protocol with fixed predefined recording times and projection angles cannot be executed.

A known solution to this problem is to prepare a protocol by means of which during a C-arm rotation X-ray images are generated in close temporal succession. On the basis of this imaging protocol, projection data sets for generating a solid model are ascertained via calibration. By means of the imaging protocol, X-ray images of the heart are then obtained which show the heart in different phases. In the meantime, an electrocardiogram signal is recorded at the same time. Subsequently, on the basis of the EKG signal (EKG—electrocardiogram), those X-ray images are then identified and selected in which the heart is shown in the desired phase. The other X-ray images are discarded. A disadvantage of this solution is that a wide variety of X-ray images is required, which is reflected in an undesirably high dose of radiation for the patient.

SUMMARY OF INVENTION

An object of the present invention is therefore to enable the generation of a solid model of a heart in a predefined phase of its periodic cardiac movement using a lower dose of radiation.

The object is achieved by a method and a C-arm X-ray unit as claimed in the independent claims. Advantageous developments of the invention are provided by the dependent claims.

The method according to the invention also enables the generation of the solid model by means of a C-arm X-ray unit. In the process, X-ray images for a solid model are generated in a single C-arm rotation, as a result of which the recording time is considerably shorter in an advantageous manner. The C-arm rotation expediently comprises at least one angular field of 180° plus the fan beam arc of the X-ray fan beam of the C-arm X-ray unit.

During C-arm rotation, an electrocardiogram signal is monitored by an EKG trigger. As expected, the EKG signal has consecutive RR intervals. During each RR interval, a trigger signal for generating at least one digital X-ray image is always transmitted to the C-arm X-ray unit (EKG triggering) by the EKG trigger as soon as the EKG signal indicates that the heart is in the predefined phase or shortly before it. In other words, triggering takes place within each RR interval, as soon as a time difference between the current phase and the predefined phase is smaller than a predefined value. The X-ray images are therefore made depending on the beat of the heart, as it is detected on the basis of the EKG signal, and therefore free from a predefined protocol unlike in the prior art. As a result, the method is particularly flexible as attention must only be paid to the path of the EKG signal, in other words, pure EKG triggering takes place. No additional boundary conditions regarding prepared imaging protocols must be met.

The generation of the solid model from several of the X-ray images now takes place in such a way that at least one X-ray image is selected from each RR interval. As the C-arm has at least rotated between the recording times, it is hereby ensured that mappings of the heart from a sufficient number of different projection angles are used to obtain an exact mapping of the heart in the solid model.

It is now a question of ascertaining the appropriate projection data sets for the X-ray images. In the method according to the invention, to this end another value for at least one parameter is ascertained for each X-ray image, said value influencing the geometry of the C-arm X-ray unit as it is to be taken into consideration in the calculation of the solid model for the reconstruction of the trajectories. In particular, for each X-ray image at least one of the following parameters is ascertained: an orientation of the C-arm, a rotational speed of the C-arm, a position of an X-ray focus of the X-ray source, a shape of the C-arm. The shape of the C-arm can, for example, be registered with strain gauges. The other parameters can be registered using the known methods.

A projection data set for the calculation of the solid model can now be ascertained in the method according to the invention, as for each X-ray image at least one parameter regarding the geometry of the image has been ascertained, since by this means several different options explained in detail below are produced to ascertain the necessary projection data sets, in other words, for example, suitable projection matrices for a backprojection.

Before the ascertaining of the parameter sets is started, however, first of all developments of the method aimed at improving the image quality are described.

A development of the method provides that during the C-arm rotation, a control signal for a pacer is generated. Within the scope of the invention, a pacer is understood to mean a heart pacemaker the electrodes of which are inserted into the heart or are applied to the heart temporarily or permanently. The pacer may, for example, comprise two catheters between which an electric current is generated for pacing. In connection with the method according to the invention, the use of a pacer has the advantage that the heart beats in a reproducible manner. Thus, X-ray images with regular, predefined angular distances of the projection angles can be obtained.

Pacers are known from the prior art in a different connection, namely cardiac valve operations, in which pacers are used to make the heart stop during a particular part of the operation by enforcing a heart rate of 200 bpm (beats per minute) and the heart then only continuing to twitch with a small movement amplitude. In the development of the method according to the invention, on the other hand, the control signal is now adapted to generate an enforced heart rate of 130 bpm or less than 130 bpm. The advantage of this is that the heart continues to perform a natural pumping movement. Longer recording times are possible without physical strain for the patient.

The heart rate should be as close as possible to the natural heart rate in the process. However, it must not be lower as otherwise this will result in the enforced heart rate being superimposed on the natural heart rate. A heart rate which is as natural as possible and nonetheless controlled is produced in accordance with an embodiment of the method by first ascertaining the so-called spontaneous heart rate, in other words the natural heart rate, from the electrocardiogram signal and then setting the artificial, enforced heart rate at a value that is higher by only one particular differential value than the spontaneous heart rate. The differential value is in particular less than 20 bpm. The heart thus performs a natural heart movement and nonetheless beats with predictable regularity.

The enforced heart rate may, for example, be used to adjust the heart rate to an existing protocol. Thus an embodiment of the method provides for generating a simulated electrocardiogram signal for a predefined heart rate by means of an EKG simulator. On the basis of the simulated electrocardiogram signal, an imaging protocol is generated for the C-arm X-ray unit in the predetermined phase for which the solid model is to be generated, since the recording timepoints for the phase can be ascertained by means of the simulated electrocardiogram signal. Thus, using the C-arm X-ray unit at least one of the required projection data sets can be ascertained in the manner described using calibration by means of the imaging protocol and a calibration body. To use the projection data sets generated with this imaging protocol, the predefined heart rate can then be reproduced from the EKG simulation in a real heart by means of a pacer. The C-arm X-ray unit is then only controlled by EKG triggering again.

As small a dose of radiation as possible per RR interval can be achieved if only a single X-ray image is generated in the RR interval. A corresponding embodiment of the method provides for generating this single X-ray image per RR interval on each occasion when the current phase, as it may be observed by means of the EKG signal, corresponds to the predetermined phase. This results in a very precise resolution of the X-ray images in terms of time. The heart is reproduced at precisely the time when it is in the predetermined phase. Preferably only a single respective X-ray image is generated in all RR intervals. Thus, fewer than 40 X-ray images in total are preferably produced during the C-arm rotation which, on the one hand, are sufficient for the creation of a solid model and, on the other hand, only subject the heart to a low dose of radiation.

As already indicated in the introduction, during an RR interval provision may also be made to generate several X-ray images. The corresponding embodiment of the method according to the invention provides for generating the X-ray images within a time slot or interval with a predefined duration which is smaller than the RR interval itself. In particular, it is provided for that the time slot is less than 50% of the RR interval. Naturally, it is hereby provided for that the predetermined phase is within the time slot. In addition, it is hereby provided for that within the time slot X-ray images are only generated at those times when the C-arm X-ray unit is in a position in which the generation of an X-ray image is also provided for by a predetermined imaging protocol. To this end, at least one aforementioned parameter is observed regarding the geometry of the C-arm X-ray unit and an X-ray image is always then generated if at least one parameter has a value which indicates that a prepared projection data set from an imaging protocol exists and therefore an X-ray image can be generated. This embodiment of the method has the advantage that in spite of EKG triggering, it is possible to have recourse to prepared protocols which were generated without EKG triggering.

Another embodiment of the method provides for the selection of suitable projection data sets for the selected X-ray images for the solid model in a database with prepared projection data sets by means of a searching device. The compliance of at least one parameter ascertained for each X-ray image with database keys provided in the database, i.e. corresponding parameters which were saved with the prepared projection data sets, serves as a search criterion. The prepared projection data sets may, for example, be those which were obtained by means of an imaging protocol which, as already mentioned in the introduction, provides for the constant generation of a wide variety of X-ray images during a C-arm movement. Then there is a high probability that the projection data sets obtained in a calibration by means of this protocol may also include those which are required to process the X-ray images taken in the time slot. In contrast to the prior art, here X-ray images are only generated within the time slot and not constantly, as actually provided for by the imaging protocol.

In the event that no suitable projection data set exists, a development of the method provides for a suitable projection data set to be interpolated from at least two projection data sets for a selected X-ray image for at least one RR interval by means of an interpolation device.

In similar fashion, the problem may arise that although several X-ray images were generated within a time slot, none of them was generated at precisely the time of the predetermined phase. To this end, an embodiment of the method provides for the interpolation of an X-ray image from at least two X-ray images by means of an interpolation device at the time of the predetermined phase.

In both the aforementioned cases, the interpolation device may in particular be designed to perform weighted superimposition of the respective data for interpolation.

Each of the previously described options for the ascertaining of suitable projection data sets provides for recourse to projection data sets which were obtained in the context of calibration. On the other hand, another embodiment of the method according to the invention provides for suitable projection data sets to be obtained solely from the data of the selected X-ray images themselves. To this end, first of all a projection matrix is provided for each selected X-ray image, as already described. This serves as a provisional projection data set for the X-ray image. Each projection matrix represents a parameterized version of the trajectories of the X-rays. The data of the projection matrices can also be combined to form a single overall projection matrix. The form of the provision is not important for the invention.

The projection matrices are altered in an iterative optimization process based on an image-based cost function until the desired accuracy of mapping of the heart is achieved in the solid model.

To this end, first of all a provisional solid model is calculated from the selected X-ray images by backprojection by means of the projection matrices. Then a shape of an object displayed in the provisional solid model, for example a catheter, is compared with a known target shape of the object. Thus, a distortion in the image can be detected immediately. Instead of a catheter, another cylindrical object can also be identified in the provisional solid model and its shape examined. As the target shape of such a cylindrical object, in particular its circular cross-sectional profile is then used. As a rule, this is sharply distorted in the case of projection matrices which have not yet been adjusted. Usually the distorted cross-sectional profile may exhibit the shape of a crescent moon.

For the adjustment of the projection matrices, the projection matrices are altered iteratively and the provisional solid model recalculated with the altered projection matrices each time until the shape complies with the target shape. Compliance need not be perfect. Provision may also be made for at least one error measure describing the difference between the shapes to be smaller than a predetermined value. The adjusted projection matrices then finally form the projection data sets for the calculation of the actual solid model.

The aforementioned comparison of the shapes may be realized in a number of ways. An embodiment of the method provides for the comparison of an eccentricity of the shape of the object mapped in the solid model with an eccentricity of the target shape. In particular, the ratio of a maximum and a minimum diameter of the respective shape can be calculated as an eccentricity value. However, other diameter values can also be used in the ratio, for example. This embodiment of the method has the advantage that a comparison is only made with a few geometric values, making a rapid calculation of the error measure possible.

In addition, or as an alternative, a template-based comparison may be made. A template of a known, real cross-sectional profile of the object is used as the target shape here. For the comparison, the template of the shape observed in the provisional solid model is superimposed. The projection matrices are then altered until the template and the observed shape are congruent or at least the difference is smaller than a predetermined error measure. The template can be created by measuring the object if, for example, it is a catheter, or also calculated by means of a model of the object.

The actual alteration of the provisional projection matrices as a function of the error measure, i.e. the difference between the shapes, is then performed in a manner known per se, for example, by means of a gradient descent method.

A development of the method for the iterative adjustment of the projection matrices enables a significant acceleration as the provisional solid model is only calculated using image data from relatively small sections of the selected X-ray images. The sections comprise the mapping of the object examined for the adjustment of the projection matrices in the respective X-ray images: for example, if the shape of a catheter is examined in the provisional solid model, then correspondingly only the image of the catheter is converted into a solid model by the backprojection as a section. As the iterative reconstruction method for adjustment need only be performed with a low volume of data, speed-optimized adjustment of the projection matrices is made possible.

As aforementioned, the invention also includes C-arm X-ray equipment. This has a C-arm X-ray unit and a control device for the C-arm X-ray unit. The latter is designed to execute an embodiment of the method according to the invention by means of the C-arm X-ray unit.

BRIEF DESCRIPTION OF THE DRAWINGS

The invention is described again in detail below on the basis of concrete exemplary embodiments. These show.

DETAILED DESCRIPTION OF INVENTION

The examples represent preferred embodiments of the invention.

In the examples explained hereafter, the components of the embodiments described and the steps of the methods described each represent individual features of the invention to be considered independently of each other, which each also develop the invention independently of each other and thus are also to be considered as part of the invention individually or in a combination other than those shown. Furthermore, the embodiments described can also be supplemented by further of the features of the invention already described.

Figure 1:
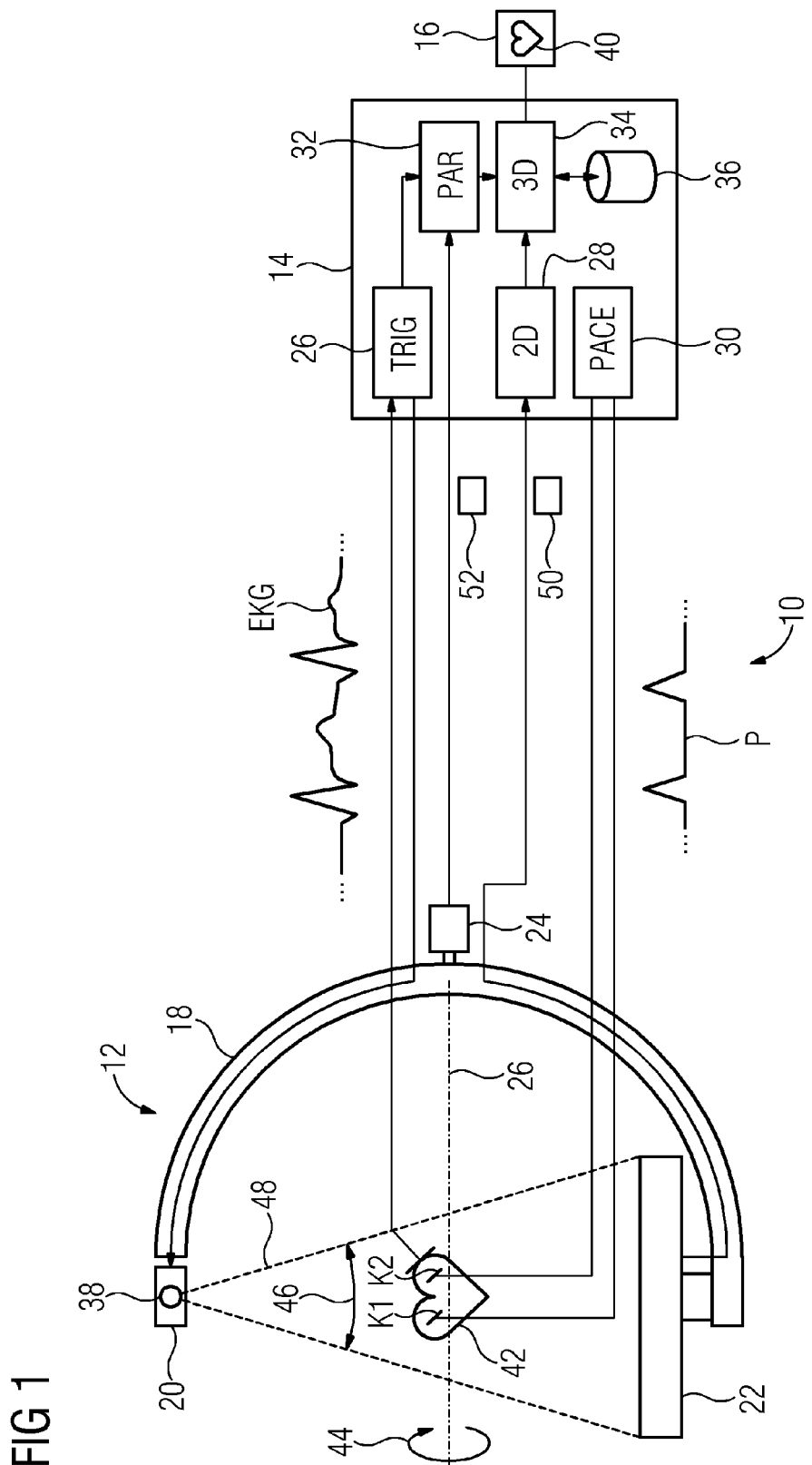
FIG. 1 A schematic representation of an embodiment of the C-arm X-ray equipment according to the invention, FIG. 2 A flow chart of a work flow of a cardiological examination in which an embodiment of the method according to the invention is embedded, FIG. 3 A schematic representation of an EKG signal, FIG. 4 A diagram of recording times which are ascertained by means of the EKG signal, FIG. 5 A sketch to illustrate image positions, FIG. 6 A sketch to illustrate the geometry of an X-ray image, FIG. 7 A flow chart of an embodiment of the method according to the invention, FIG. 8 An additional flow chart of the method of FIG. 7, FIG. 9 An additional EKG signal and FIG. 10 A diagram to illustrate recording timepoints which are determined on the basis of the EKG signal of FIG. 9.

FIG. 1 shows C-arm X-ray equipment 10 comprising a C-arm X-ray unit 12, a control unit 14 for the C-arm X-ray unit 12 and a display device 16.

The C-arm X-ray unit 12 has a C-arm 18, a controllable X-ray source 20, an X-ray detector 22, for example a flat-panel detector, and a drive 24 by means of which the C-arm is rotated around a rotational axis 26. The C-arm X-ray unit 12 may, for example, be the product DynaCT® from Siemens AG.

The control device 14 may, for example, be a computer or a system consisting of several computers. It may comprise: a trigger module 26 for evaluating an EKG signal and triggering an X-ray image, a receive module 28 for receiving 2D X-ray image data from the X-ray detector 22, a pacer module 30, a parameter recording module 32, which receives operating parameters from the C-arm X-ray unit 12, for example from the drive 24, and a rendering module 34 for generating a solid model from 2D image data which the rendering module 34 receives from the receive module 28. The modules 26 to 34 may, for example, be provided as programs belonging to the control device 14. The control device may furthermore comprise a database 36 in which projection data sets can be saved. Each projection data set represents a mapping rule by means of which from the 2D X-ray image data of a digital X-ray image, the X-ray image can be combined with additional X-ray images to form a solid model by the rendering module 34. For example, each of the projection data sets may comprise values for one or more projection matrices, as known per from the prior art, for example in connection with backprojection. However, a projection data set may also comprise other data which in a comparable manner describes a beam path of X-rays from an X-ray focus 38 of the X-ray source 20 to the pixels of the X-ray detector 22, wherein data for a known rotary orientation and preferably also a known rotational speed of the C-arm 18 is specified. The solid model generated from the rendering module 34 can be displayed by the display device 16. The display device 16 may, for example, be a monitor.

In this example a solid model 40 of a heart 42 is to be generated by means of the C-arm X-ray equipment 10. The heart 42 beats and performs a periodic pumping motion in the process. The solid model 40 is intended to represent the heart 42 in a particular movement phase or phase C0 of the pumping movement. However, another periodically moving object can also be examined by means of the C-arm X-ray equipment 10, for example, a material sample.

To generate the solid model 40, the C-arm 18 is rotated in a single rotational movement or C-arm rotation 44 around the rotational axis 26 by the drive 24. The C-arm rotation 44 comprises e.g. an angle of 180° plus a fan width 46 of an X-ray fan 48, as it is radiated by the X-ray source 20 during the generation of an X-ray image in a recording area of the X-ray detector 22. The C-arm rotation 44 may also comprise a larger angle. During the C-arm rotation 44, an EKG signal EKG is recorded in the heart 42 and transmitted to the control unit 14. The trigger module 26 observes the EKG signal EKG and always triggers an image e.g. by controlling the X-ray source 20, as soon as the trigger module 26 detects from the EKG that the heart 42 is in the phase C0 or shortly before. The X-ray detector 22 then generates digital 2D image data which represents an X-ray projection or X-ray image 50 of the heart 42. The X-ray image 50 is transmitted from the X-ray detector 22 to the receive module 28. For the X-ray image 50, the parameter recording module 32 can receive a current rotary orientation of the C-arm 18, for example from the drive 24 as a parameter 52.

During the C-arm rotation 44, the pacer module 30 can generate a control signal P which is then transmitted to a pacemaker or pacer which comprises two catheters K1, K2 which have electric contacts and which can be inserted into the heart 42. By means of the control signal P, the heartbeat of the heart 42 is set to a predetermined heart rate, in other words a particular heart rate is enforced.

After the C-arm rotation 44 has finished, the rendering module 34 generates the solid model 40 from the X-ray images 50. The rendering module 34 can ascertain the projection data sets required for this by means of the parameters 52 which it receives from the parameter recording module 32. The calculated solid model 40 displays the rendering module 34 e.g. by means of the display device 16.

The mode of operation of the C-arm X-ray equipment 10 is explained again in detail hereafter on the basis of the additional figures.

FIG. 2 illustrates a work flow W which e.g. can be performed by a physician who would like to generate the solid model 40 by means of the C-arm X-ray equipment 10. The following steps are performed for this:

S10: Establishment of the phase C0 which is to be represented by the solid model 40. For example, the value 70% RR of an RR interval of the EKG can be selected as the phase C0 (see FIG. 3 for illustration).

S12: Generation of the control signal P for the pacer (catheters K1, K2), wherein preferably a heart rate of 130 bpm or less than 130 bpm is set, with the selected heart rate being higher than the spontaneous heart rate.

S14: Injection of a contrast agent into a pulmonary artery, a ventricle of the heart, a vena cava, a ventricle or another blood-perfused vessel.

S16: Awaiting the arrival of the bolus of the contrast agent in the heart 42, it being possible to monitor the arrival by means of a fluoroscopic examination or a DSA (digital subtraction angiography). On arrival of the bolus, manual starting or automatic starting of C-arm rotation 44.

S18: Automated generation of X-ray images 50 during C-arm rotation 44 as a function of the EKG signal (image acquisition).

S20: Calculation of the solid model 40 by the rendering module 34.

The steps S10, S12 and S14 may also be executed in a sequence other than that described.

Figure 5:
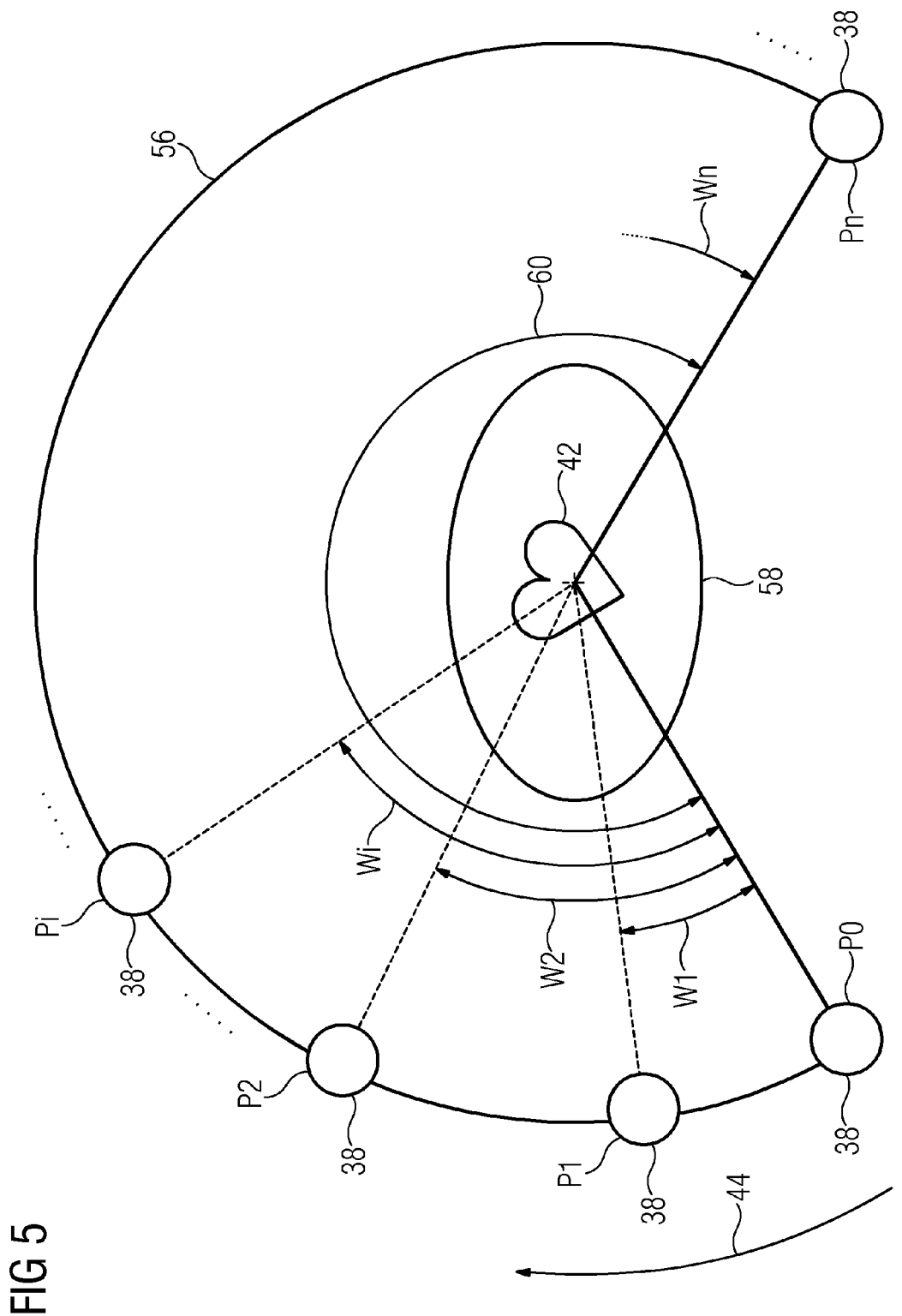

The step S18 of image acquisition is explained in more detail again hereafter on the basis of FIG. 3, FIG. 4 and FIG. 5. It is assumed that in the step S10, C0=70%–RR was determined as the phase to be displayed.

In FIG. 3 the path of the EKG is plotted again over the time t, as it is received by the trigger module 26. The EKG exhibits consecutive RR intervals in the known manner. By means of the EKG the trigger module 26 detects the time at which the phase C0 occurs. In the example forming the basis of FIG. 3, FIG. 4 and FIG. 5, a single control pulse 54 is generated by the release module 26 at the time of the phase C0 and is transmitted to the X-ray source 20. With this "single-pulse principle" (single-pulse recording), an X-ray image 50 is generated at the time of each phase C0. In FIG. 4 the chronological position of the trigger pulse 54 with regard to the phase C0 in an RR interval is illustrated again for this purpose. At the time of the phase C0, a trigger signal is switched from a minimum level MIN to a maximum level MAX. This applies to every RR interval.

In FIG. 5 a respective spatial position of the X-ray focus 38 is shown for the individual trigger pulses 54. The associated spatial position of the X-ray detector 22 is of course opposite the X-ray focus 38 on the other side of the heart 42. FIG. 5 shows an idealized, circular trajectory 56 of the X-ray focus 38 during the rotational movement 44.

The C-arm rotation 44 is started as soon as e.g. the phase C0 is detected in the EKG by the trigger module 26 for the first time. By means of the trigger pulse 54 then generated, a projection P0 of the heart 42 in the body 58 is generated in the X-ray detector 22 and transmitted to the receive module 28 as a first digital X-ray image 50. During the further path of the EKG, the C-arm 18 rotates with the X-ray source 20 and the X-ray detector 22 in accordance with the C-arm rotation 44. As soon as the phase C0 occurs again, a trigger pulse 56 is generated by the trigger module 26 again and a further projection P1 is generated. Almost the same time lags are produced between the X-ray images by the regular control signal P of the pacer module 30 for the additional consecutive projections P2 to Pn respectively. In total, n+1 X-ray images are generated, for example 30 images. In other words, projections Pi exist, wherein the index i has values from 0 to n, with n=29. The time lags correspond to the duration of the RR interval as it is enforced by the pacer module 30 in the heart 42.

The subtended total angle of rotation 60 here is at least 180° plus the fan beam arc 46. The consecutive projection angles Wi, with index i=0 to n, differ due to the regular heartbeat and a constant rotational speed of the C-arm 18 respectively around the same differential angle.

The C-arm X-ray unit 12 need not adhere to a particular imaging protocol during the C-arm rotation 44. It is therefore possible for the physician to freely select the desired phase C0 in step S10. A geometry determination for the single-pulse technique is described below on the basis of FIG. 6, FIG. 7 and FIG. 8. The image times are heart-rate-dependent. Therefore the projection angles W1 to Wn are also heart-rate-dependent. For this reason the typical calibration scenarios described in the introduction do not work. In addition, the speed of C-arm rotation 44 must be set to heart-rate-dependent, as a minimum number of projections is required for a high-quality reconstruction of the shape of the heart 42 in the solid model 40. Preferably thirty X-ray images 50 are made.

Both the rotary orientation and the speed of the C-arm 18 are responsible for the geometric parameters of the C-arm X-ray unit 12. The geometric parameters describe, for example, a rotation of the X-ray detector 22 or a displacement of the same, if for instance the C-arm 18 is stressed differently under the weight of the components depending on rotary orientation and bends as a result. The geometric parameters therefore influence the projection data sets necessary for the calculation of the solid model 40. This is illustrated again below by FIG. 6.

Figure 6:
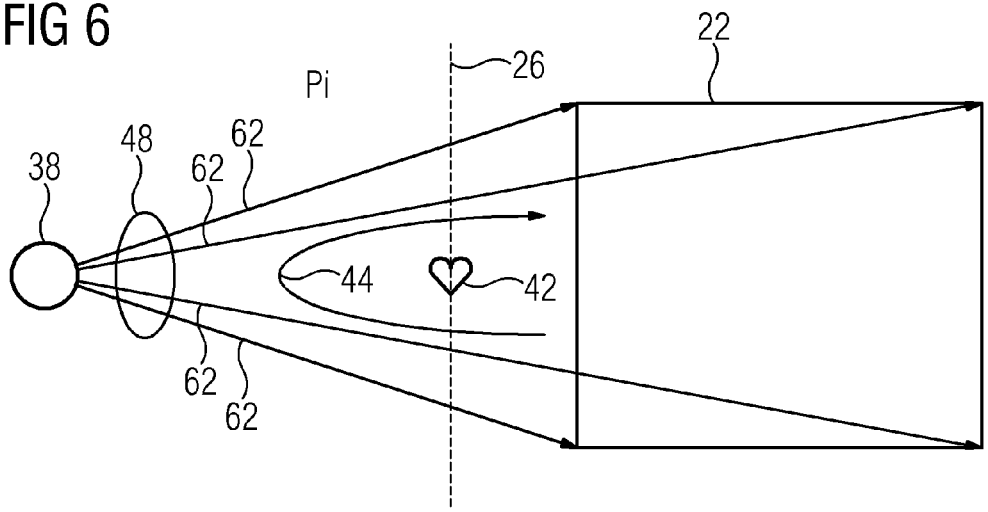

FIG. 6 shows the geometry of a projection Pi for one of the X-ray images, wherein i stands for a value of 0 to n here. During the C-arm rotation 44 around the rotation axis 26, the projection Pi is generated at a particular rotary orientation Wi and at a particular speed, by generating X-rays in the X-ray focus 38 which strike the X-ray detector 22 along trajectories 62 in the beam fan 48 through the heart 42. In FIG. 6 only four trajectories 62 are shown as examples.

To generate the solid model 40, the trajectories 62 must be reconstructed in such a way that the geometry is correctly reconstructed for the individual voxels. Even a displacement of the X-ray focus 38 with respect to the X-ray detector 22 by 0.5 mm or 1 mm causes such a serious distortion of details in the range of 1 mm$^3$ that these are no longer comparable with the actual anatomical circumstances.

Figure 7:
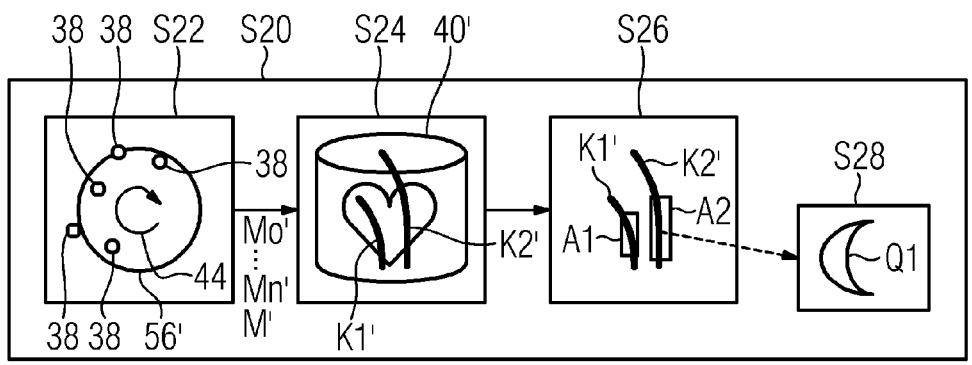

A geometry calibration in accordance with the first alternative is described below on the basis of FIG. 7 and FIG. 8. This calibration does not require any prepared projection data sets.

In a step S22, so-called circular-path fitting can optionally be performed, as described by Kyriakou et al. ("Simultaneous misalignment correction for approximate circular cone-beam computed tomography", Pys. Med. Biol. 53, 2008, pages 6267 to 6289). This results in provisional projection data sets which here are preferably provisional projection matrices M0' to Mn' (in other words, Mi' with index i=0 to 29) for a backprojection of the n+1 X-ray images 50. The provisional projection matrices M0' to Mn' can also be obtained from rough estimates as the rotational speed of the system, the frame rate and the angular field are known from the images as this data was recorded by the parameter recording unit 23. A single large provisional total projection matrix M' can also be provided as a provisional projection data set in which all the projection data corresponding to the projection data sets from the individual matrices M0' to Mn' is contained. It is assumed hereafter that several single provisional projection matrices M0' to Mn' are provided.

A provisional solid model 40' is generated in a step S24 from the provisional projection matrices M0' to Mn'. In spite of the distortions still present, image labels are clearly identifiable therein, thus for example metal objects. In interventional cardiology or electrophysiology e.g. typically mappings K1', K2' of the catheters K1, K2 or other electrodes are present in the vicinity of or inside the heart 42. Thus, for instance, a coronary sinus, electrodes pertaining to pacemakers or a so-called pigtail for the injection of contrast agent. These objects are used here as image labels for calibration. In the case of the catheters K1, K2 and similar electrodes, it may be assumed here that their geometry is cable-like, i.e. that they have coiled, cylindrical bodies. It is important here that a circular cross-section is available. The detection of the images K1', K2' can, for example, take place by means of threshold-value-based segmentation as metal electrodes generate very high values as 3D-image data in the provisional solid model 40'. In the case of additional assumptions about the cable-like shape of the catheters K1, K2, so-called region growing or a similar method, which are known per se from the prior art, can also be used. For the mappings K1', K2', their centerlines are also defined. This can be done using methods known per se from the prior art. The centerlines describe the path of the central axes of the catheters K1, K2 along their longitudinal extension.

In a step S26 those sections A1, A2 of these objects whose longitudinal extension axis of cylindrical shape lies parallel to the rotational axis 26 are detected in the provisional solid model 40' by the rendering module 34. Instead of the rotational axis 26, another predetermined axis can also be used for orientation. The sections A1, A2 do not need to be perfectly parallel to the selected axis; a deviation at a predetermined angle may also be permitted, for example, 10° or 5°. Classification and sorting may also be performed according to the degree of parallelism. The selected sections A1, A2 are then used for calibration.

If the geometry calibration is not correct, i.e. the matrices M0' to Mn' are not suitable for a sufficiently precise reconstruction of the heart 42 in the solid model 40, this is discernible in the cross-section of the sections A1, A2 of the mappings K1', K2' of the catheters K1, K2. In a step S28 it is correspondingly checked whether a cross-section Q1 of the section A1 and correspondingly also a cross-section (not shown) of the section A2 is actually circular. In this case, FIG. 7 shows how a crescent-moon-shaped cross-section Q1 can be produced if the provisional projection matrices M0' to Mn' are not yet adjusted to the actual geometry of the C-arm unit 12. The cross-section Q1 therefore represents an uncalibrated catheter image in cross-section. A good estimate of the projection geometry would produce near-circular cross-sections. The more X-ray images 50 with different projection angles W0 to Wn are considered, the more precise the estimate which is described hereafter.

Figure 8:
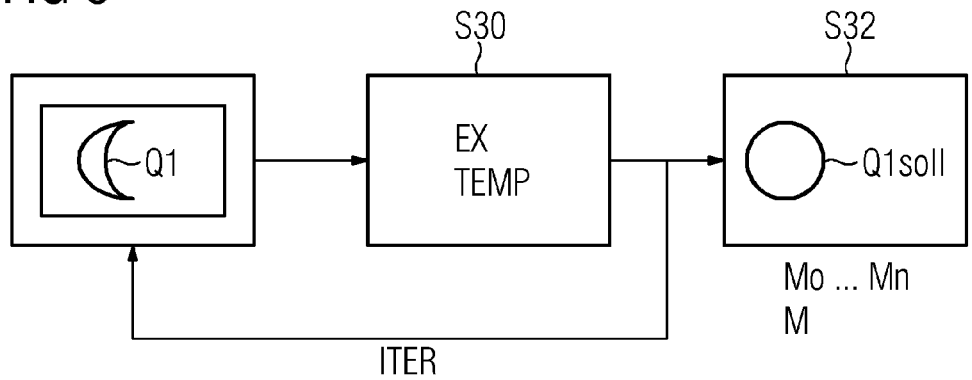

FIG. 8 describes an iterative alteration and optimization of the matrices M0' to Mn', with a cost function being optimized. The cross-section of the catheter K1, i.e. the cross-section Q1, is isolated in a step S30 by thresholding (threshold value detection) and the eccentricity E calculated for the cross-section Q1 obtained. E indicates the extent to which the segmented cross-section resembles a circle. The smallest and the largest cross-section of the circle can be used as the error criterion for optimization. As an alternative to the eccentricity, a comparison of the cross-sections Q1 with a template $Q1_{soll}$ of the ideal catheter cross-section can be performed, e.g. by means of template-matching known from the prior art. The template $Q1_{soll}$ can, for example, be calculated by modeling the catheter on the basis of a-priori information.

Both alternatives of the comparison produce an error measure, so-called costs. To minimize these costs, the projection matrices M0' to Mn', for example, are now altered by means of a gradient descent method or a similar method of optimization by means of a cost function known per se. In an additional iteration ITER the provisional solid model 40' is now recalculated and a new cross-section Q1 generated. This process is repeated until the cross-section Q1 corresponds to the template $Q1_{soll}$ or the eccentricity corresponds to that of a circle. Then the matrices generated in this way are used as final projection matrices M0 to Mn or as a total projection matrix M for the calculation of the final solid model 40 from the X-ray images 50.

The solid model 40' may also only be a partial reconstruction which only maps the catheter area. Speed-optimized iteration is made possible by this means, as only a small volume needs to be calculated.

In a second alternative, a pre-calibration with an EKG trigger simulation, or EKG simulation for short, can be enabled. As pacing always produces an identical and reproducible cardiac movement for all heartbeats, with the aid of an EKG simulator, as can be acquired as the product "Sensis", for example, an artificial EKG can be generated and fed into the trigger module 26. The trigger module 26 accepts the artificial EKG and triggers the trigger pulses correspondingly for a pre-set phase C0. The duration of the RR intervals is essential for the triggering; the precise shape of the EKG is not relevant here. The system can therefore be pre-calibrated offline for each heart rate and heart phase, as the measuring positions are reproducible in spite of triggers by the pacing.

Figure 10:
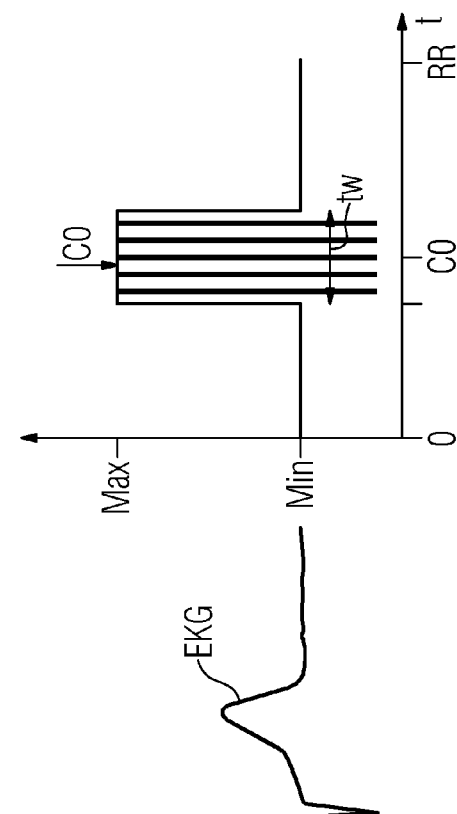
Figure 9:
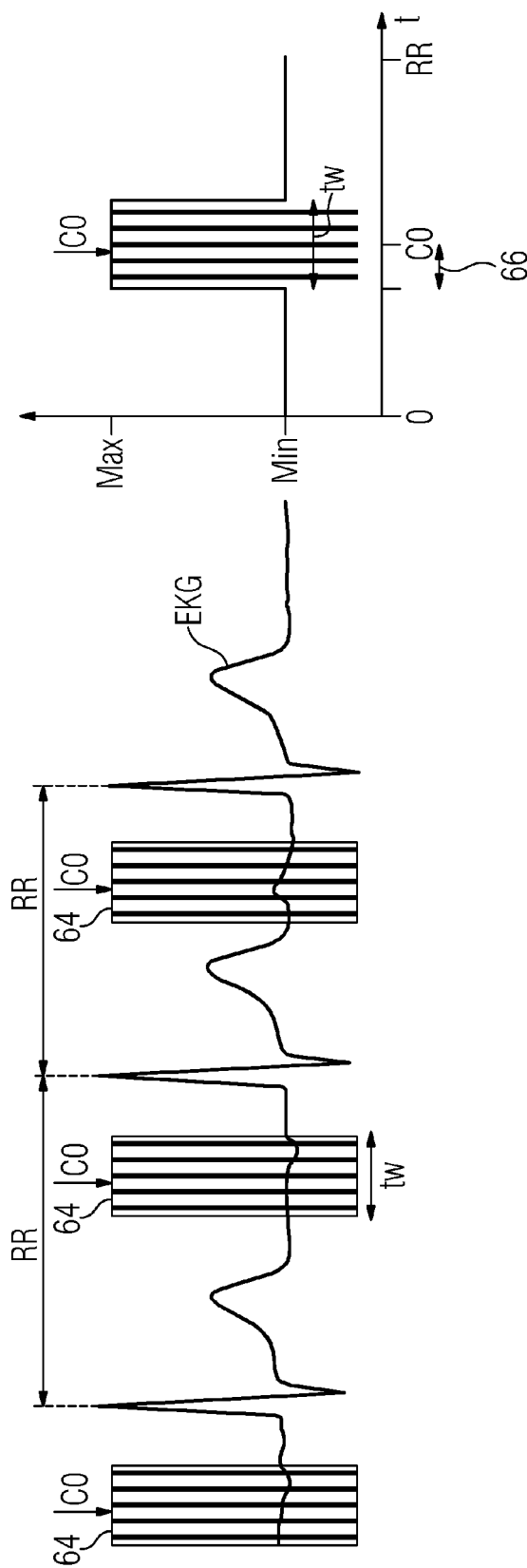

In a third alternative a database search in the database 36 and an interpolation between projection tables can be undertaken. This is explained again on the basis of FIG. 9 and FIG. 10. So as not to have to calibrate all the cardiac phases separately, at the same heart rate and therefore the same rotational speed first of all untriggered image acquisition with many projections can be performed regardless of a predetermined phase at close angular distances and corresponding projection data sets generated for this purpose by means of a calibration body. Alternatively, projection data sets can also be used, such as, for example, geometry tables for the geometry of the C-arm X-ray unit 12, which are brought together from different databases and saved in the database 36. After generation of the X-ray images 50 and saving of the parameters 52, suitable projection data sets can then be selected by the rendering module 34 from the database 36 by means of the parameters.

With the third alternative, it is therefore possible to resort to a standard imaging protocol again. The known image positions, for which projection data sets are available in the database 36, can be correlated with the EKG and the best possible match sought. For this purpose, for each phase C0, i.e. in each RR interval, not only single image pulses, but instead several image pulses can also be generated in a time slot 64 with a duration tw around the phase C0. The image window 64 begins a predetermined period 66 each time before reaching the phase C0. The image pulses are only generated for those projection angles for which corresponding projection data sets have already been filed in the database 36.

For missing projection data sets it is also possible to interpolate between adjacent positions.

Iterative optimization of the geometry can also be added to the method of the third alternative, as already described in connection with FIG. 6 to FIG. 8.

The invention enables the prospective triggering of a scan, i.e. the recording of X-ray images for the imaging of a solid model which can be performed from the outset without a preceding C-arm rotation. It is all performed in only one rotation and can be supported by heart pacing. A 3D solid model of the heart is produced during a particular cardiac phase, e.g. 70% RR. The pacing can be selected very slowly in the process, giving rise to a normal but nonetheless reproducible cardiac movement which is optimal for a multi-segment reconstruction which results in the solid model.

Radiation is only triggered for the corresponding phase (single pulse) or in a predetermined time slot (pulsing window). In the time slot continuous exposure does not take place but single pulses continue to be triggered. Weighting of the images enables interpolation between two pulses.

In particular, prospective triggering, for example by means of a cardiac DynaCT, is made possible by the method. As a result there is a significant reduction in the number of X-ray images taken. Typically, only 30 projections are necessary. This results in a significantly lower dose of radiation for the patient. The EKG triggering makes high temporal resolution possible. The X-ray images are all made during a single pass of the C-arm, which produces considerable benefits in terms of practicability compared with multiple pass. In particular, the images can be obtained in a shorter period. The iterative determination of the geometry by means of image labels enables online-calibration for each image data set, which is enabled by an image-based cost function. Offline calibration is also possible, as with the aid of pacing the heartbeat is always reproducible. Iterative construction methods can be applied by a correspondingly small selected provisional solid model to a low volume of data, which results in the acceleration of this reconstruction. The single pulse technique makes a significantly lower dose possible with simultaneously improved temporal resolution, as each image pulse is triggered in precisely the desired phase. With the pulsing window technique, on the other hand, it is possible to resort to standard geometry so that no additional calibration is required. Here only a correlation with the recorded EKG is required. Suitable weighting and interpolation can also result in reduced noise here. Multi-segment reconstruction can combine single heartbeats better, as the heartbeats can be predicted with great precision by means of the pacing due to reproducibility. As the C-arm rotation can comprise an angle of 180° plus fan beam arcs without any problem, no monitoring of angle consistency is required.

The invention claimed is:

1. A method for generating a solid model of a heart in a predetermined phase of a periodic pumping movement of the heart, comprising:
    observing an electrocardiogram signal which exhibits consecutive RR intervals by an EKG trigger during a single C-arm rotation of a C-arm X-ray unit;
    generating digital X-ray images in each of the RR intervals by the C-arm X-ray unit with the EKG trigger as soon as a time difference between a current phase and a predetermined phase is less than a predetermined value;
    determining a parameter influencing a geometry of the C-arm X-ray unit for each of the X-ray images; and
    generating the solid model from the X-ray images,
    wherein at least one X-ray image is selected from the each of the RR intervals,
    wherein a projection data set is determined for the selected X-ray image for generating the solid model by the parameter, and
    wherein a projection matrix is provided for the selected X-ray image, wherein a provisional solid model is calculated based on the projection matrices by backprojection, wherein a shape of an object mapped in the provisional solid model is compared with a target shape of the object, wherein the projection matrix is altered iteratively and the provisional solid model is recalculated until the shape matches the target shape or at least a difference between the shape and the target shape is smaller than a predetermined value, and wherein the altered projection matrix is used as the projection data set.

2. The method as claimed in claim 1, wherein the parameter is selected from the group consisting: a rotational orientation of the C-arm X-ray unit, a rotational speed of the C-arm X-ray unit, a position of an X-ray focus of the C-arm X-ray unit, and a shape of the C-arm X-ray unit.

3. The method as claimed in claim 1, wherein a control signal for a pacer is generated which is designed to generate an enforced heart rate of 130 bpm or less than 130 bpm during the C-arm rotation.

4. The method as claimed in claim 3, wherein a spontaneous heart rate is ascertained from the electrocardiogram signal and the control signal is displayed which is greater than the spontaneous heart rate by a predetermined differential value, and wherein the differential value is less than 20 bpm.

5. The method as claimed in claim 1, wherein a simulated electrocardiogram signal for a predefined heart rate is generated by an EKG simulator, wherein an imaging protocol is generated for the C-arm X-ray unit in the predetermined phase based on the simulated electrocardiogram signal, and wherein the projection data set is determined by the imaging protocol and a calibration body.

6. The method as claimed in claim 1, wherein only a single respective X-ray image is generated in at least one of the RR intervals, wherein the single X-ray image is generated at a time at which the current phase matches the predetermined phase, and wherein overall fewer than 40 X-ray images are generated during the C-arm rotation.

7. The method as claimed in claim 1, wherein several respective X-ray images are generated in at least one of the RR intervals, wherein the several respective X-ray images are generated in a time slot which has a predetermined duration less than the RR interval and comprising the predetermined phase, and wherein within the time slot the parameter is observed and an X-ray image is generated if the parameter has a value for which a prepared projection data set exists.

8. The method as claimed in claim 1, wherein a suitable projection data set is selected by the parameter using a searching device in a database with prepared projection data sets for the selected X-ray image.

9. The method as claimed in claim 1, wherein a suitable projection data set is interpolated from two projection data sets or an X-ray image is interpolated from two X-ray images at the predetermined phase for at least one of the RR intervals for the selected X-ray image by an interpolation device, wherein the interpolation device performs weighted superimposition for the interpolation.

10. The method as claimed in claim 1, wherein the object is a cylindrical catheter, wherein a cylindrical shape of the cylindrical catheter is examined and used as the target shape, and wherein the target shape is a circular cross-sectional profile of the cylindrical shape.

11. The method as claimed in claim 1, wherein an eccentricity of the shape is compared with an eccentricity of the target shape and is respectively calculated as an eccentricity value, and wherein the eccentricity value is a ratio of a maximum and a minimum diameter of the shape.

12. The method as claimed in claim 1, wherein a template of a cross-section profile of the object is used as the target shape, and wherein the template is geometrically superimposed with the shape observed in the provisional solid model.

13. The method as claimed in claim 1, wherein the provisional solid model is only calculated with image data of a respective section in which the object is reproduced.

14. A C-arm X-ray equipment, comprising:
    a C-arm X-ray unit; and
    a control device adapted to perform a method comprising:
        observing an electrocardiogram signal which exhibits consecutive RR intervals by an EKG trigger during a single C-arm rotation of a C-arm X-ray unit;

generating digital X-ray images in each of the RR intervals by the C-arm X-ray unit with the EKG trigger as soon as a time difference between a current phase and a redetermined chase is less than a predetermined value;
determining a parameter influencing a geometry of the C-arm X-ray unit for each of the X-ray images; and
generating the solid model from the X-ray images,
wherein at least one X-ray image is selected from the each of the RR intervals,
wherein a projection data set is determined for the selected X-ray image for generating the solid model by the parameter, and
wherein a projection matrix is provided for the selected X-ray image, wherein a provisional solid model is calculated based on the projection matrices by backprojection, wherein a shape of an object mapped in the provisional solid model is compared with a target shape of the object, wherein the projection matrix is altered iteratively and the provisional solid model is recalculated until the shape matches the target shape or at least a difference between the shape and the target shape is smaller than a predetermined value, and wherein the altered projection matrix is used as the projection data set.

* * * * *